United States Patent [19]
Yallampalli et al.

[11] Patent Number: 5,910,482
[45] Date of Patent: Jun. 8, 1999

[54] TREATMENT OR PREVENTION OF PREECLAMPSIA, ECLAMPSIA WITH CALCITONIN GENE RELATED PEPTIDE, CGRP ANALOG, PROGESTATIONAL AGENT, NITRIC OXIDE SOURCE, AND CYCLOOXYGENASE INHIBITOR

[75] Inventors: Chandrasekhar Yallampalli, Houston; Sunil J. Wimalawansa, Friendswood, both of Tex.

[73] Assignee: Board of Regents, The University of Texas System, Austin, Tex.

[21] Appl. No.: 08/619,841

[22] Filed: Mar. 19, 1996

[51] Int. Cl.$^6$ ................................................. A61K 31/04
[52] U.S. Cl. ............................................. 514/12; 530/307
[58] Field of Search ................................ 514/12; 530/307

[56] References Cited

U.S. PATENT DOCUMENTS

| | | | |
|---|---|---|---|
| 4,393,226 | 7/1983 | Witiak et al. | 549/433 |
| 5,364,841 | 11/1994 | Cooper et al. | 574/12 |
| 5,508,045 | 4/1996 | Harrison et al. | 514/509 |
| 5,595,970 | 1/1997 | Garfield et al. | 514/12 |
| 5,612,314 | 3/1997 | Stamler et al. | 514/13 |
| 5,622,973 | 4/1997 | Morriello et al. | 514/318 |

FOREIGN PATENT DOCUMENTS

| | | |
|---|---|---|
| WO 95/02408 | 1/1995 | WIPO . |
| WO 95/13800 | 5/1995 | WIPO . |
| WO 95/13802 | 5/1995 | WIPO . |

OTHER PUBLICATIONS

Shew et al., Biosis AN 93:87984, 1993.
Fiscus, Caplus AN 1994:183589.
Tan, Medline AN 95136728, Oct. 1994.
Pennefather, Caplus AN 1990:605182.
Shew et al. "Role of Nitric Oxide in CGRP Relaxation" Peptides, v. 14, pp. 637–641, 1993.
International Search Report dated Jul. 30, 1997 (UTFG:216P).
Supowit et al., "Calcitonin Gene–Related Peptide is a Depressor in L–Name—Induced Preeclampsia," *50th Annual Fall Conference and Scientific Sessions of the Council for High Blood Pressure Research*, Chicago, Illinois, Sep. 17–20, 1996.
Yallampalli et al., "Calcitonin Gene related Peptide Reverses Hypertension and Decreases the Fetal Mortality Associated with L–Name–Infusion in Pregnant Rats," *Society for Gynecological Investigation*, Abstract No. 504, Philadelphia, Mar. 20–23, 1996.
Yallampalli et al., "Calcitonin Gene–Related Peptide Reverses the Hypertension and Significantly Decreases the Fetal Mortality in Pre–Eclampsia Rats Induced by $N^G$–Nitro–L–Arginine Methyl Ester," *Human Reproduction*, 11(4):895–899, 1996.

*Primary Examiner*—Cecilia J. Tsang
*Assistant Examiner*—Patrick R. Delaney
*Attorney, Agent, or Firm*—Arnold White & Durkee

[57] ABSTRACT

The present invention provides a method for counteracting preeclampsia, eclampsia of pregnancy and preterm labor in a pregnant female mammal treated by administering thereto calcitonin gene-related peptide (CGRP) or its analogues including CGRP/adrenomedullin or their peptide or receptor-based analogues, or in combination with a progestin, and with or without a nitric oxide substrate, or a nitric oxide donor or both, optionally in further combination with one or more of a cyclooxygenase inhibitor, a $PGI_2$-mimetic, a thromboxane ($TXA_2$) inhibitor, a compound possessing $TXA_2$-agonistic, and $TXA_2$-inhibiting properties, a compound possessing $TXA_2$-antagonistic and $PGI_2$-mimetic activities, and a $TXA_2$ antagonist. CGRP, progesterone and some of the nitric oxide substrate and donor compounds are naturally occurring compounds. As such these agents do not have the same toxicity and allergy problems as the foreign substances that are currently used for similar purposes. During pregnancy uterine blood vessels and the uterine muscles are particularly sensitive to CGRP as well as nitric oxide. Therefore, one could administer a very small quantities of these drugs (i.e., intravenously, subcutaneous, or Implants), the effects are then seen mainly in the uterine muscle and blood vessels, namely increase the blood supply to the uteroplacental unit (hence nutrients and oxygen supply to the fetus through the improved placental circulation), and uterine muscular relaxation thereby ameliorate the signs and symptoms of preeclampsia, and eclampsia, and prevent preterm labor. At these dosages, virtually no systemic effects are induced, making CGRP (which is an endogenous natural product present in human body) extremely safe and effective.

32 Claims, 5 Drawing Sheets

FIG. 1A (SEQ ID NO:1)

FIG. 1B (SEQ ID NO:2)

TREATMENT OR PREVENTION OF PREECLAMPSIA, ECLAMPSIA WITH CALCITONIN GENE RELATED PEPTIDE, CGRP ANALOG, PROGESTATIONAL AGENT, NITRIC OXIDE SOURCE, AND CYCLOOXYGENASE INHIBITOR

BACKGROUND OF THE INVENTION

This invention relates to a method for the treatment of preeclampsia and of preterm labor with calcitonin gene-related peptide (CGRP) or CGRP/CGRP receptor-based analogue and combinations with a progestational agent (with or without a nitric oxide synthase substrate such as L-arginine, a nitric oxide donor or both), alone or in further combination with one or more of a cyclooxygenase inhibitor, a $PGI_2$-mimetic, a thromboxane ($TXA_2$) inhibitor, A compound possessing $TXA_2$-agonistic and $TXA_2$-inhibiting properties, a compound possessing $TXA_2$ antagonistic and $PGI_2$-mimetic activities, and a $TXA_2$ antagonist, and to pharmaceutical compositions comprising such a combination.

Preeclampsia, toxemia, or eclampsia of pregnancy can be significant health problems during pregnancy and are the leading causes of fetal growth retardation, fetal mortality, premature birth, and maternal mortality. The etiology of this pathology is largely unknown and effective therapy is not available. Preeclampsia of pregnancy is characterized by a triad of hypertension, pathological edema and proteinuria. This disease affects 6 to 10% of all pregnancies.

Nitric oxide (NO) has been shown to be the endothelium derived relaxing factor (EDRF) generated from the endothelium of blood vessels. Nitric oxide is a major mediator in the control of vascular relaxation. Nitric oxide is synthesized from L-arginine by nitric oxide synthase located in endothelial and other cells. Nitric oxide can also be generated by application of various nitric oxide donors such as sodium nitroprusside, nitroglycerin, SIN-1, isosorbid mononitrate, isosorbid dinitrate, and the like.

Treatment of pregnant rats with nitric oxide synthase inhibitors, e.g., analogues of L-arginine such as $N^G$-nitro-L-arginine methyl ester (L-NAME), results in elevated blood pressure, fetal growth retardation and proteinuria. Thus, inhibition of nitric oxide synthesis produces conditions and symptoms identical to preeclampsia of pregnancy and indicates that preeclampsia is the direct result of the decrease in nitric oxide synthesis and/or a change in the regulation of vascular tone. These condition give rise to increased blood pressure, decreased blood flow to the fetus, retarded fetal development, and proteinuria. Agents that raise nitric oxide levels therefore are useful in the treatment of preeclampsia of pregnancy. Nitric oxide donors also reduce uterine contractility during pregnancy and are useful for treating preterm labor. The nitric oxide effects of CGRP on blood pressure (BP) may be dependent upon the activation of guanylate cyclase and generation of cGMP to produce relaxation.

OBJECTS OF THE INVENTION

One object of the present invention to provide a method for the treatment of preeclampsia and prevention of preterm labor with a combination of CGRP and a progestational agent with or without a nitric oxide source such as a nitric oxide synthase substrate and/or direct NO donor. It is another object to provide such a method in which a CGRP or its synthetic agonists is used in combination with a progestational agent for the prevention and treatment of preeclampsia and preterm labor. A further object is the provision of pharmaceutical compositions useful in practicing the methods of this invention. Other objects will be apparent to those skilled in the art to which this invention pertains.

SUMMARY OF THE INVENTION

This invention provides methods for treating preeclampsia and preterm labor in a pregnant mammal. This method comprises administering to a pregnant female manifesting symptoms of such conditions a composition comprising at least one of (a) CGRP (a naturally occurring vasorelaxant peptide present in human body), CGRP analogue, CGRP receptor analogue (peptide or non-peptide), adrenomedullin or adrenomedullin receptor analogue, (b) a progestational agent, and (c) possibly a nitric oxide synthase substrate (L-arginine and the like) and a nitric oxide donor, alone or in further combination with one or more of a cyclooxygenase inhibitor, a $PGI_2$-mimetic, a thromboxane ($TXA_2$) inhibitor, a compound possessing $TXA_2$-agonistic and $TXA_2$-inhibiting properties, a compound possessing $TXA_2$ antagonist and $PGI_2$-mimetic activities, a $TXA_2$ antagonist, and receptor blockers for vasoconstrictors such as angiotensin II receptor antagonist (e.g., Losartane). The amount of CGRP administered is bioequivalent to 0.25–1 nmol bolus dose or 2–10 pmol/kg/minute as an infusion, or slow release or depot preparation of CGRP, CGRP analogue or CGRP receptor-based peptide or peptide mimetic (i.e., orally administrable) analogue form in the amounts effective to ameliorate the symptoms and signs. Although L-arginine is the established substrate of nitric oxide synthase substrate should other whole substrates be found, they are considered the equivalent of L-arginine for purposes of the present invention. When the term "CGRP" is used, for example in the appended claims, it is understood that this may be αCGRP, βCGRP (or both), a CGRP analogue having similar biological activity or the like. Any nucleophilic or other nitric oxide adducts that liberate nitric oxide under physiological conditions are viewed as nitric oxide donors of the present invention.

The amount of the progestational agent administered is bioequivalent to 50–300 mg of injected progesterone and the amount of the nitric oxide synthase substrate, nitric oxide donor or both is effective to, respectively, either raise the blood level of circulating L-arginine in a pregnant female to whom the composition is administered by at least about 1 mM above the normally 2 to 3 mM circulating L-arginine levels. Since, CGRP, nitric oxide, and progesterone are all naturally occurring compounds in the human body, these substances will not cause the same toxicity and allergenic problems, as contrasted with many foreign substances (i.e., various drugs) that are currently used for similar purposes.

In another aspect, this invention relates to a method of treating preterm labor in a pregnant female which comprises administering to a pregnant female manifesting symptoms of preterm labor, effective amounts of (a) CGRP, CGRP analogue or CGRP receptor-based peptide or non-peptide analogs, or CGRP/amylin/adrenomedullin receptor analogue (b) a progestational agent, (c) with or without a nitric oxide synthase substrate and a nitric oxide donor effective to terminate the preterm labor, alone or in further combination with one or more of a cyclooxygenase inhibitor, a $PGI_2$-mimetic, a thromboxane ($TXA_2$) inhibitor, a compound possessing $TXA_2$-agonistic and $TXA_2$-inhibiting properties, a compound possessing $TXA_2$-antagonistic and $PGI_2$-mimetic activities, and a $TXA_2$ antagonist, the amount of the progestational agent administered being bioequivalent to 50–300 mg of injected progesterone and the amount of the nitric oxide synthase substrate, nitric oxide donor both being effective to, respectively, either raise the blood level of circulating L-arginine in a pregnant female to whom the composition is administered to at least about 1 mM above the normally 2 to 3 mM circulating levels, or raise nitric oxide donor levels to about 1 to 100 nM or to an amount of nitric oxide produced by such elevated L-arginine levels.

In an important aspect, this invention relates to a method of treating preterm labor in a pregnant female which comprises administering to a pregnant female manifesting the symptoms thereof, an amount of pharmaceutical composition comprising (a) CGRP and one or more of (b) a progestational agent and (c) possibly a nitric oxide synthase substrate and a nitric oxide donor, alone or in further combination with one or more of a cyclooxygenase inhibitor, a $PGI_2$-mimetic, a thromboxane ($TXA_2$) inhibitor, a compound possessing $TXA_2$-agonistic and $TXA_2$-inhibiting properties, a compound possessing $TXA_2$-antagonistic and $PGI_2$-mimetic activities, and a $TXA_2$ antagonist. The amount of the progestational agent administered is bioequivalent to 50–300 mg of injected progesterone and the amount of the nitric oxide syntheses substrate, a nitric oxide donor or both being effective to, respectively, either raise the blood level of circulating L-arginine in a pregnant female to whom the composition is administered to at least about 1 mM above the normally 2 to 3 mM circulating levels, or raise nitric oxide donor levels to about 1 to 100 nM or donate about the same amount of NO that such elevated arginine levels could produce.

In another aspect, this invention relates to a pharmaceutical composition comprising (amounts per unit dosage of) (a) CGRP, adrenomedullin peptide, or CGRP receptor analogue and (b) a progestational agent and (c) possibly a nitric oxide synthase substrate and/or a nitric oxide donor, alone or in further combination with one or more of a cyclooxygenase inhibitor, a $PGI_2$-mimetic, a thromboxane ($TXA_2$) inhibitor, a compound possessing $TXA_2$-agonistic and $TXA_2$-inhibiting properties, a compound possessing $TXA_2$-antagonistic and $PGI_2$-mimetic activities, and a $TXA_2$ antagonist. The amount of the progestational agent per unit dosage is bioequivalent to 50–300 mg of injected progesterone and the amount of the nitric oxide synthase substrate, a nitric oxide donor or both per unit dosage being effective to, respectively, either raise the blood level of circulating CGRP to at least about 15 pmol/L above the normally 5–25 pmol/L circulating levels.

DESCRIPTION OF THE INVENTION

The methods of the invention are used to treat one or more of preeclampsia and preterm labor in a pregnant female mammal, including a human, who is manifesting the symptoms thereof or who is a high risk candidate for doing so, e.g., as determined by the progress of a present or previous pregnancy.

During pregnancy CGRP effects on blood pressure and uterine relaxation appear to be progesterone-dependent because CGRP was especially effective during pregnancy when progesterone levels are elevated. These effects were abolished after delivery of fetus. Thus, combinations of CGRP with progesterone are particularly efficacious for the treatment of preeclampsia and prevention of preterm labor. The actions of these agents, namely CGRP, progesterone, and nitric oxide are augmented in the presence of a cyclooxygenase inhibitor and angiotensin II receptor antagonists (e.g., $AT_1$ antagonists such as Losartane).

Because these abnormal conditions of pregnancy are produced by or aggravated by subnormal nitric oxide synthesis, both nitric oxide synthase substrates, e.g., L-arginine, and nitric oxide donors, e.g., sodium nitroprusside, nitroglycerin, glyceryl trinitrate, SIN-1, isosorbidemononitrate and isosorbidedinitrate, are useful for ameliorating the symptoms thereof. In one aspect of the method of this invention, a combination of both are employed. A synergistic effect is achieved when a progestational agent is administered concurrently with CGRP with or without nitric oxide synthase substrate and/or nitric acid donor.

CGRP is a 37-amino acid neuropeptide which is the most potent naturally occurring vasodilator peptide in the human body. CGRP is distributed throughout the central and peripheral nervous systems, and is found in areas known to be involved in cardiovascular function (Wimalawansa S. J., Calcitonin gene-related peptide, calcitonin, amylin and adrenomedullin: a peptide super family, Critical Reviews in Neurobiology, in press, 1996). CGRP is present in uterus, specially around the uterine arterial system. In addition, CGRP is found in nerve fibers that form a dense periadventitial network throughout the uterine perivascular system. CGRP has prominent relaxant effects on vascular and other smooth muscle cells. The pregnant uterine smooth muscles are particularly sensitive to CGRP which may play an important role in uterine quiescent during pregnancy (Nelson S. H., Steisland, O. S., and Suresh, M. S. Possible physiological role of calcitonin gene-related peptide in the human uterine artery. Am J. Obs. Gynecol. 168: 605–611, 1993).

Figure 1A:
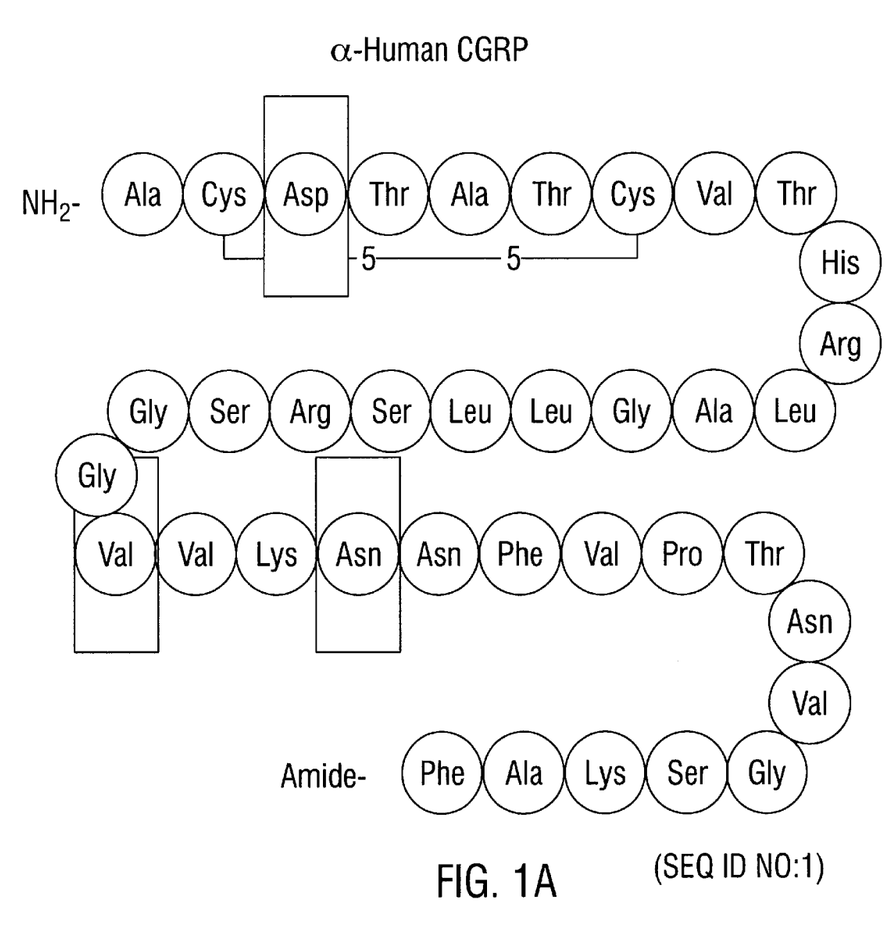
FIG. 1 Schematic amino acid sequence of human α and β CGRP.
Figure 1B:
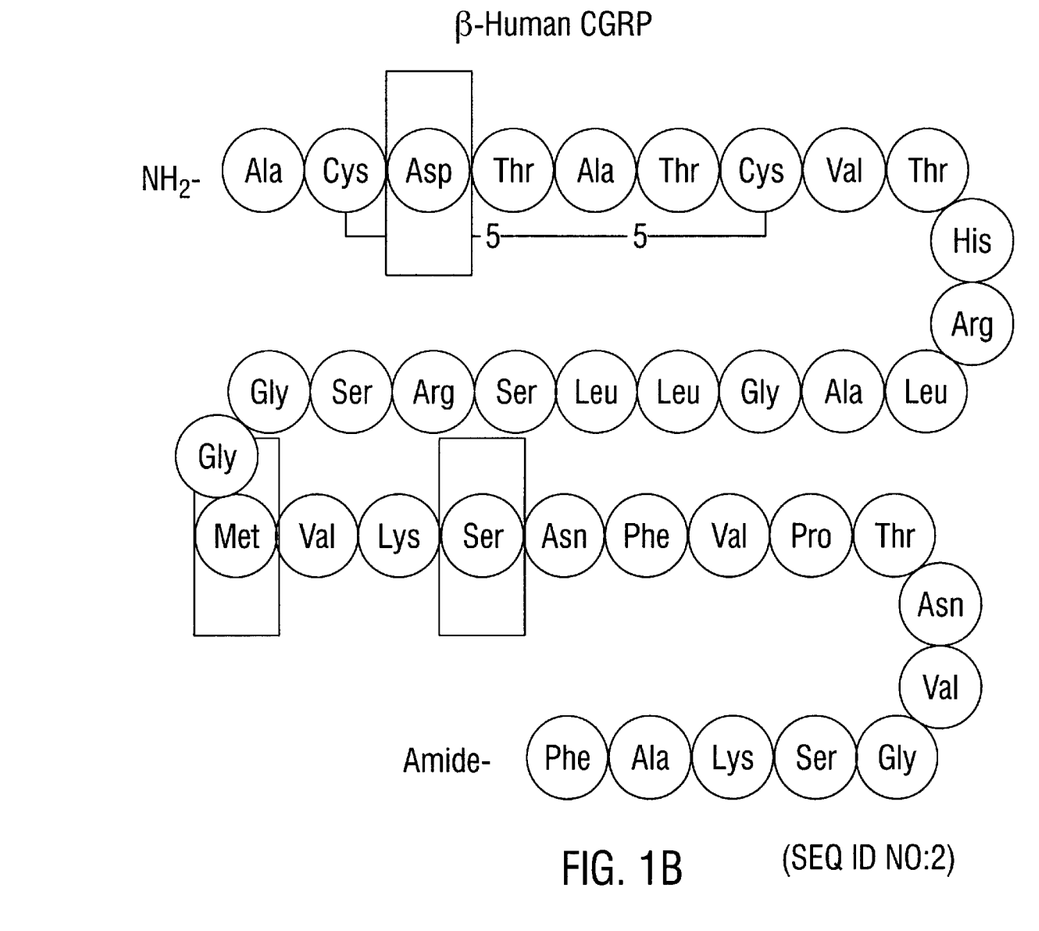

CGRP occurs in two known forms ($\alpha$ and $\beta$) in the human. The $\alpha$- form is shown in SEQ ID NO. 1 and the $\beta$- form is shown in SEQ ID NO. 2. The $\alpha$- and $\beta$- strains of CGRP both are present in plasma, cerebrospinal fluid, and the spinal cord. Wimalawansa, S. J., Morris, H. R., MacIntyre, I. J. Mol. Endocrinol., 3:247 (1989). Both forms have been isolated and fully characterized by amino acid sequencing and fast atom bombardment-mass spectrometry (FABMS); Wimalawansa, S. J., Morris, H. R., Etienne, A., Blench, I., Panico, M., and MacIntyre, I. Isolation, purification and characterization of b -hCGRP from human spinal cord, Biochem. Biophys. Res. Commun., 167, 993 (1990); Steenberg, et al. FEBS Letts. 183:403 (1985), incorporated herein by reference. Genes for CGRP have been identified on chromosome 11. Hoopener, et al. Hum. Gen. 70:259 (1985). CGRP receptors have been isolated and purified, and monoclonal antibodies have been raised against these purified receptors. Wimalawansa, S. J. Isolation and characterization of calcitonin gene-related peptide receptors and raising monoclonal antibodies. Wimalawansa, S. J. Annals of New York Academy of Sciences, Vol. 657:7087 (1992); Wimalawansa, S. J., Gunasekera, R. D., Zhang, F. Isolation, purification, and characterization of calcitonin gene-related peptide receptor. Peptides 14:691–699 (1993); Proccedings, First International Symposium on Calcitonin Gene-Related Peptide. Graz., Austria, Regul. Peptides. 14, 691. (1993); and Wimalawansa, S. J. Calcitonin gene-related peptide, calcitonin and amylin: a peptide super family. Crit. Rev. Neurobiol. (in press), incorporated herein by reference.

The preferred form of CGRP for use in the present invention is CGRP that is synthesized using an automatic peptide synthesizer using well known methods. The amino acid sequence of CGRP is known, and the $\alpha$- and $\beta$- forms are represented in SEQ. ID NOS. 1 and 2, respectively. In the human, the $\alpha$- and b - forms of CGRP represented in SEQ. ID NOS. 1 or 2 differ in structure by only three amino acids, and each possesses equal biological activity in the cardiovascular system.

A preferred method for synthesizing the CGRP is the well known Merrifield method. Merrifield, R. B. J. Am. Chem. Soc. 85:2149 (1963); Merrifield, R. B. Science, 232:341 (1986), both incorporated herein by reference. See also Wimalawansa, S. J. Use of synthetic peptides in specific affinity chromatography for purification of specific peptide receptors. Innovation and Perspectives in solid Phase synthesis (Peptides, Polypeptides and Oligonucleotides), (Ed.) R. Epton, Intercept Ltd., Andover, UK (1991) 111–119, incorporated herein by reference. Either t-Boc, F-Moc, or fast-Moc solid-phase peptide chemistry may be used to synthesize the peptide. However, CGRP or its analogues including receptor-based peptide or non-peptide analogues can be synthesized using other methods in addition to solid-phase technology of peptide synthesis.

Once synthesized, the authenticity of the resulting peptide may be verified using known procedures, such as fast atom bombardment mass spectroscopy, amino acid sequencing and analysis. After synthesis, the peptide preferably should be filter sterilized (0.2 mm), aliquoted, lyophilized, and stored in sterile ampoules or in catheters. Just prior to application, the lyophilized powder should be dissolved in sterile normal saline (0.9% NaCl in water).

Synthetic human CGRP also may be obtained commercially, e.g. from: Peninsula Laboratory, located in Belmont, Calif.; Bachem Biosciences, Inc., located in King of Prussia, Pa.; and, Sigma Chemicals, located in St. Louis, Mo. Commercial grade human CGRP is not marketed for human use; therefore, commercially available human CGRP's may be used in the present invention only if they are purified and sterilized so that they are fit for human use (GNP grade). CGRP can be delivered to the target blood vessel or tissue as an authentic compound or as a liposomal form. Genetically engineered human CGRP also may be used in the present invention. Similar results also could be achieved using a CGRP analogue (i.e., agonist) or peptide or non-peptide mimetic analogue based on the CGRP, amylin or adrenomedullin "receptor structure." These include "peptide-based" analogues, as well as "peptide-mimetic" analogues of simple structure (i.e., for oral use) (e.g.: through combinatorial libraries). Animal-derived CGRP's are biologically active (often equivalent to human CGRP) and thus could be used in the present invention; however, as a practical matter, animal-derived CGRP's may present allergy and autoimmune problems and therefore preferably should be avoided.

The route of administration of the CGRP will vary depending upon the contemplated application. For the present method and invention, the CGRP or its analogues (peptide or receptor-based) can be administered by intravenous, subcutaneous, transdermally implanted pellet, or liposomal depot/preparations, slow releasing disposable mini pumps, intra-arterial application, buccal, nasal, rectal or oral route. The dose of CGRP in humans should be between about 0.1 and 2 nmol administered as a bolus dose, or preferable as an infusion of 1–15 pmol/kg/minute. The CGRP may be in either free or liposomal form. The dose can be pre-loaded into a catheter suitable for insertion into the target artery for local administration of the dose. However, in order to make the CGRP as economical as possible and practical, variable doses also may be used, preferable via a second channel in the catheter. In the vast majority of patients may benefit from simple intravenous dosage or through an implantable mini pumps or by other means. However analogues of CGRP/amylin/adrenomedullin or their receptor-based peptide or non-peptide analogues can be given in any route including sublingually transdermally and orally.

In summary, CGRP can be infused or delivered, 0.1 to 2 nmol of free or liposomal form intravenously, or 25% of the same dose, directly to the target artery as a bolus dose. Alternately, 1 to 15 pmol/kg/minute of the CGRP may be infused locally into the target artery through the catheter. In order to make the product as economical as possible in the case of an arterial catheter is used, the catheter should be adapted for infusion of a second dose or infusions locally to the target artery. In some cases, it may be beneficial for the intravenous or local infusion of CGRP to last for a longer period of time after the initial bolus dose. (e.g: a low dose intravenous infusion of 50–200 pmol/kg/hr of CGRP is recommended, provided that the blood pressure is satisfactorily maintained). Depending on the reason for administration, the derivation needs to be adjusted from a simple bolus dose to several days or weeks of administration.

Where the CGRP is used to prevent preterm labor, and treatment of preeclampsia or eclampsia, the CGRP preferably should be infused into a peripheral vein at a dose of about 25–200 pmol/kg/hr for several hours, or days as appropriately, as in the case of administration of intravenous heparin or nitrates. These infusions should be repeated as necessitate by the clinical condition. For this particular use, local infusion via a catheter may not be required. In the case of preeclampsia, the action of CGRP can be further enhanced with the addition of a small dose of an anti-platelet drug, a salicylate (e.g.: aspirin), progesterone and a nitric oxide donor at or near the doses described for the treatment of preeclampsia or eclampsia of pregnancy. However, analogues of CGRP/amylin/adrenomedullin, or their receptor-based peptide or non-peptide mimetic analogues can be given in any route including sublingually and orally for this indication.

Thus, in one aspect, the method of this invention and the pharmaceutical composition of this invention involve a combination of (a) CGRP or its analogues and (b) a progestational agent, (e.g., progesterone) (c) with or without a nitric oxide donor and a nitric oxide synthase substrate and, (d) one or more of a cyclooxygenase inhibitor, [e.g., aspirin; a $PGI_2$-mimetic, e.g., iloprost and cicaprost; a thromboxane ($TXA_2$) inhibitor, e.g., dazoxiben hydrochloride (benzoic acid, 4-[2-(1H-imadazol1-yl)-ethoxy]-, monohydrochloride; UK 37248), dazmegrel (1H-indole-1-propanoic acid, 3-(1H-imidazol-1-ylmethyl)-e-methyl-; UK 3885), ozagrel (2-propenoic acid, 3-[4-(1-H-imidazol-1-ylmethyl)phenyl]-; OKY-046) and pirmagrel (imidazo[1,5-a]pryidine-5-hexanoic acid; CGS-13080); a compound possessing $TXA_2$-agonistic and $TXA_2$-inhibiting properties, e.g, ridogrel (pentanoic acid, 5-[[[3-pyridinyl[3-(trifluoromethyl) phenyl]methylene]-amino]oxy]-; R-68070) and labogrel (6-heptenoic acid, 7-phenyl-7-(3-Pydridinyl)-; a compound possessing $TXA_2$-antagonistic and PGI2-memetic activities, e.g., 5-heptenoic acid, 7-[3-[[(diphenylmethoxy)-imino]-bicyclo,[2.2.1]hept-2-yl]-;EP 035-rac) and 5-heptenoic acid, 7-[3-[[(diphenylmethoxy)-imino]methyl]biclo[2.2.2]-oct-5-en-2-yl]-(EP 157); and a $TXA_2$ antagonist, e.g., 5-heptenoic acid, 7-[3-[[2-(phenyl-amino)carbonyl]hydrazino]methyl]7-oxabicyclo[2.2.1]hept-2-yl]-, 1S[1.alpha.,2.alpha.(Z), 3.alpha.,4.alpha.]]-(SQ 29548); benzenepropanoic acid, 2-[[3-4[(pentylamino)carbonyl]-2-oxazolyl]-7-oxabicyclo [2.2.1]hept-2-ylmethyl}(BMS 180291); acetic acid, [4-[2-[(phenylsulfonyl) amino]-ethyl]penoxy]-(sultroban, BM-13177); benzeneacetic acid, 4-[2-[[[4-chlorophenyl)

sulfonyl]amino]ethyl]-(daltroban,BM-13505); (S-145 rac); 5-hexenoic acid, 6-[3-[[[(4-bromophenyl)sulfonyl]amino] methyl]bicyclo[2.2.1]hep-2-yl]-, decyl ester, [IS [1.alpha.2.alpha.2.alpha.(Z),-3.beta.,4.alpha.]]-(ONO 8809); 9H-carbazole-9-propanoic acid, 3-[[(4-fluorophenyl) sulfonyl]amino]-1,2,3,4-tetra-hydro-, (R)-(bay-u-3405); and (4Z)-6-[(5S)-5-(4-chlor-phenylsulfonyl(aminomethyl)-cycloent-1-enyl]4-hexenoic acid (ZU 154343).

Examples of combinations of active agents which can be administered concurrently with CGRP or its analogue, or receptor-based analogues with or without a nitric oxide synthase substrate and/or a nitric oxide donor, and a progesterone (or other progestational agent) are low dose (e.g., 10–100 mg) of aspirin (or other cyclooxygenase inhibitor; PGI$_2$-mimetics (e.g., iloprost, cicaprost); combinations of a PGI$_2$-mimetic and low dose aspirin, and angiotensin II receptor (AT$_1$) antagonists. Examples of dosage ranges of typical CGRP or its bioequivalent analogues, and NO substrate and NO-donors (per os) are:

| | Total dose: |
|---|---|
| CGRP | 0.1–0.5 nmol/kg/hr (parenteral, or an equivalent doses *via* other routes including orally) |
| L-Arginine | 0.5 g–10 g (orally) |
| Sodium Nitroprusside | range 500–2000 µg/kg/day (intravenous) |
| Nitroglycerin | 0.5–10 mg (sublingual, percutaneous, *etc.*) |
| Isosorbidmononitrate | 10–100 mg |
| Isosorbiddinitrate | 10–100 mg |

The following are typical oral dosage ranges of active agents of the progestin and the optional other active agents concurrently administered with the CGRP or analogues thereof with or without nitric oxide substrate or donor:
Progestins: A daily dose bioequivalent to 50–300 mg of progesterone/day, e.g., an injectable suspension of medroxyprogersterone acetate to provide a weekly dose of thereof of 100–1000 mg or tablets or dragees providing an oral dose thereof of 5–10 mg/day; an injectable solution of hydroxyprogesterone caproate which provides a weekly dose of 250–500 mg; tablets, capsules or dragees of northindrone acetate which provide a daily dose of 5–20 mg.

Cicaprost: 5–100 µg/kg/day p.o.

Aspirin: 1–50 mg/kg/day p.o.

The pharmacologically active agents employed in this invention can be administered in admixture with conventional excipients, i.e., pharmaceutically acceptable liquid, semi-liquid or solid organic or inorganic carriers suitable, e.g., for parental or enteral application and which do not deleteriously react with the active compound in admixture therewith. Suitable pharmaceutically acceptable carriers include but are not limited to water, salt solutions, alcohol, vegetable oils, polyethylene glycol, gelatin, lactose, amylose, magnesium stearate, talc, silicic acid, viscous paraffin, perfume oil, fatty acid monoglycerides and diglycerides, pentaerythritol fatty acid esters, liposomes (e.g., mono- or poly-cationic liposomes) hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parental application, particularly suitable are solutions, preferably oily or aqueous solutions, as well as suspensions, emulsions, or implants, including suppositories. Ampoules are convenient unit dosages.

In a preferred aspect, the compositions of this invention are adapted for ingestion. For enteral application, particularly suitable are unit dosage forms, e.g., tablets, dragees or capsules having talc and/or a carbohydrate carrier or binder or the like, the carrier preferably being lactose and/or corn starch and/or potato starch; particular solids, e.g., syrups and elixirs or like, wherein a sweetened vehicle is employed. Sustained release compositions can be formulated including those wherein the active compound is protected with differentially degradeable coatings, e.g., by microencapsulation, multiple coatings, etc.

Suitable for oral administration are, inter alia, tablets, dragees, capsules, pills, granules, suspensions and solutions. Each unit dose, e.g., each tablespoon of liquid or each tablet, or dragee contains, for example, 5–5000 mg of each active agent.

Solutions for parenteral administration contain, for example, 0.01–1% of each active agent in an aqueous or alcoholic solution.

The CGRP or its analogues, and nitric oxide substrate and/or donor can be administered as an admixture with the progestational agent and any other optional active agent or as a separate unit dosage form, either simultaneously therewith or at different times during the day from each other.

The combination of active agents is preferably administered at least once daily (unless administered in a dosage form which delivers the active agents continuously) and more preferably several times daily, e.g., in 2 to 6 divided doses or as a continuous infusion/administration. The typical dose is about 0.1 to 1000 mg of each active agent, although some less active agents may be, e.g., 500 to 10,000 mg, and others, e.g., CGRP or its analogues, sodium nitroprusside, require lower doses, e.g., 10–2000 µg/kg/day. Doses for nitroglycerine typically are orally, 2.5 mg 2×daily; sublingually, 0.8 mg 1–4×daily; and transdermally, 0.2–0.4 mg/hr. Since the LD$_{50}$ dosages of most of these active agents is known in the prior art, a lower dosage regimen can be initiated and the dosage increased until a positive effect is achieved or a higher dosage regimen can initially be employed, (e.g., in a crisis situation, and the dosages regulated downward as relief from the symptoms is achieved).

In humans, both CGRP (or its peptide or non-peptide mimetic analogues) and progesterone (or bioequivalent of another progestin) and L-arginine should be given in a ratio which produces blood plasma levels of about 50 pmol/L, 300–1,000 ng/ml (0.9–3 µmol/L), and 1–5 µmol/L respectively. The NO-donor, e.g., sodium nitroprusside, should be given with the progesterone (or bioequivalent of another progestin) in a ratio producing blood plasma levels of about 1–10 µmol/L and 300–1,000 ng/ml (0.9–3 µmol/L), respectively.

CGRP requires intact whole molecule for its full agonistic biological activity. Truncation of the peptide at the N-terminus (for example removal of the N-terminal loop of the peptide) changes its activity to an antagonist (e.g. CGRP(8–37). However, smaller fragments of peptide adrenomedullin (i.e., 13–52) contains the full biological activity of this peptide on vascular tissues.

The present inventors have also modified the amino acid residues of the potential cleavage sites of the CGRP (i. e., residues 11–13 and 22–25) to inhibit biodegradation of CGRP in vivo. However, major structural modifications of CGRP then may lead not only to loss of CGRP authenticity, but also lead to immunogenecity (development of autoantibodies and subsequent loss of bio-activity). The peptide and non-peptide mimetics developed against CGRP and adrenomedullin peptides, and based upon the peptide binding sites (receptors) including CGRP, amylin and adrenomedullin will also have a similar effect to CGRP in the disorders mentioned in this application. These analogues can be of a peptide nature (e.g., designed for the three-dimensional structure of the receptor binding region of the peptide) or more effectively, peptide mimetics of simple structure such as organic molecules which can be administered by 'any route' such as oral, bucal, percutaneous, or parenteral. Since the use of CGRP itself is expensive (e.g., the cost of production, characterization, etc.), the inventors envisage that the use of the above mentioned 'non-peptide mimetic analogues' will eventually supersede the use of 'peptide based analogues'. When the term "CGRP" is used in the appended claims, it is understood to include these bioactive equivalents.

BRIEF DESCRIPTION OF THE DRAWINGS

The invention will be further understood with reference to the following figures.

DESCRIPTION OF THE PREFERRED EMBODIMENTS

CGRP was synthesized according to the Merrifield method of t-Boc solid-phase peptide chemistry. An Applied Biosystem automated peptide synthesizer was used for the synthesis, and amino acids were obtained from Applied Biosystem, Foster City, Calif. The resulting peptide was characterized by fast atom bombardment mass spectrometry, amino acid analysis, and sequencing.

Figure 2:
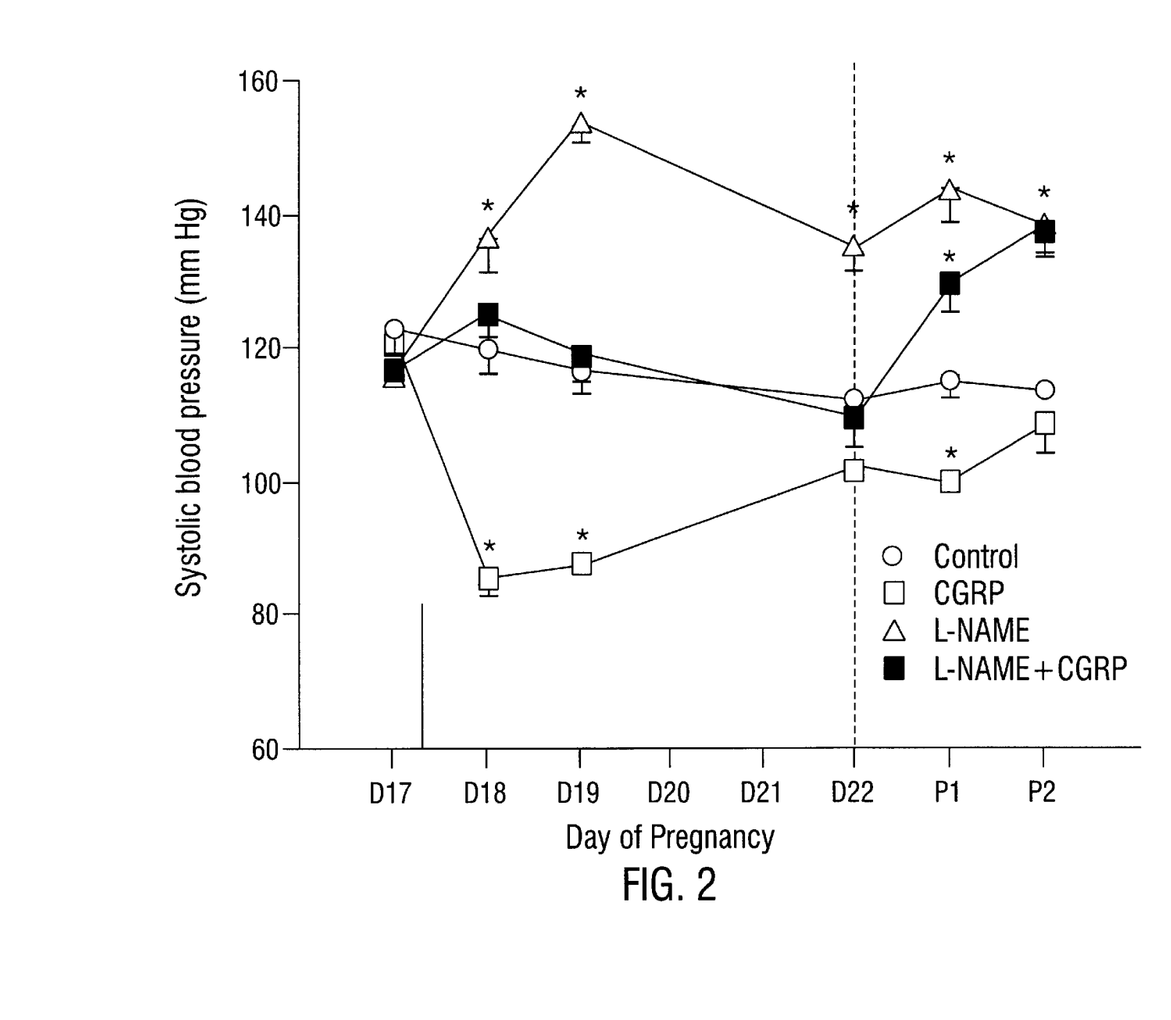
FIG. 2 A line graph showing the effect of hypertensive agent L-NAME (50 mg/rat) on blood pressure.

CGRP remedies L-NAME induced hypertension. The effects of hypertensive agent L-NAME (50 mg/rat) on blood pressure were studied. In animals treated with L-NAME and CGRP, the CGRP completely reduced L-NAME-induced hypertension, during pregnancy when progesterone levels are elevated, but not during postpartum period when progesterone levels have declined. This data indicates that beneficial effects of CGRP on preeclampsia may be controlled by progesterone. Five animals per group were treated with either: L-NAME, L-NAME+progesterone, L-NAME+ CGRP, or control (vehical only). Progesterone was injected subcutaneously (2.0 mg per rat/twice daily) from postpartum day 1 (pp-1) for 5 days. L-NAME was infused as described in the FIG. 2. Results showed that CGRP alone was ineffective during postpartum period when circulating progesterone levels are minimal. However, suppplementation of progesterone to this group of rats, completely reversed the L-NAME induced hypertension. Moreover, once the progesterone injections were stopped, the blood pressure reverted back to hypertension levels.

The data in Table 1 below show the effects of L-NAME infusion on blood pressure (mm Hg) in pregnant rats.

TABLE 1

Systolic Blood Pressure (mm Hg)

| # day | CONTROL | L-NAME 50 mg/day |
|---|---|---|
| Gestational: | | |
| Day 17 | 122 ± 3 | 116 ± 3 |
| Day 18 | 119 ± 3 | *137 ± 6 |
| Day 19 | 116 ± 3 | *154 ± 3 |
| Day 22 | 113 ± 6 | *137 ± 8 |
| Postpartum: | | |
| PP Day 1 | 115 ± 3 | *145 ± 5 |
| PP Day 2 | 114 ± 2 | *140 ± 5 |

Means with asterisks differ significantly from controls on respective days. L-NAME was infused from day 18 of gestation (*P < 0.05, n = 5).

The data in Table 2 below show the delivery day and the pups survival following delivery of L-NAME infusion to pregnant rats.

TABLE 2

| Variable | CONTROL Group | L-NAME 50/mg/day |
|---|---|---|
| Day of Delivery | 22 ± 0 | 22 ± 0 |
| Total # of pups | 49 | 55 |
| # of dead pups | 0 | 10* |
| Weight of pups (g) | 6.2 ± 0.06 | 5.14 ± 0.07* |
| Total # of animals | 5 | 5 |

*P < 0.05

Figure 3:
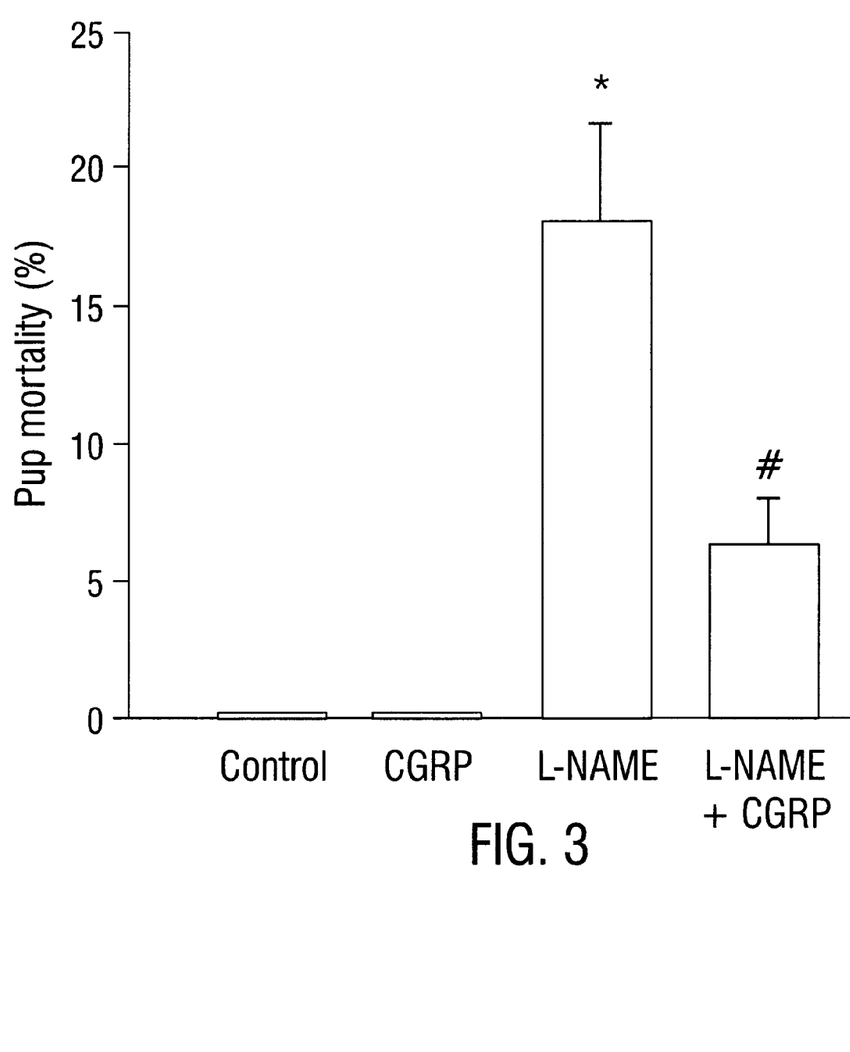
FIG. 3 A bar chart which shows the effect of these agents described in the FIG. 2 on pup survival rate (5 rats per group).
Figure 4:
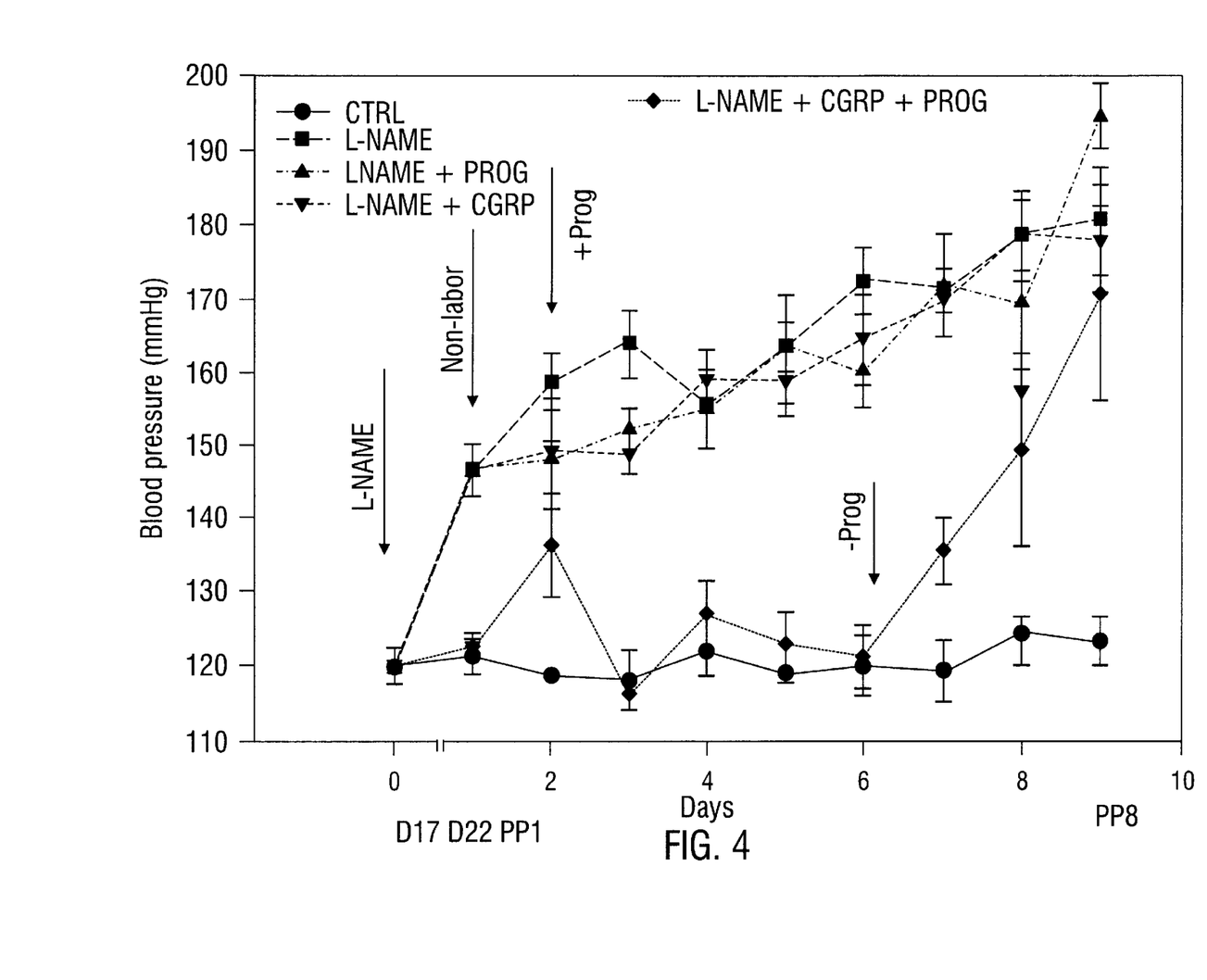
FIG. 4 A line diagram showing the role of progesterone in modulating CGRP effects on blood pressure during the postparum period.

Evaluation of fetal mortality, one of the features of preeclampsia (FIG. 3) indicates that treatment of "preeclamptic" animals with CGRP significantly improves the fetal survival rate. Thus CGRP and CGRP/amylin/ adrenomedullin or their receptor-based peptide or non-peptide agonists compounds administered to "preeclamptic" group of animals provides a highly significant advantage to survival of the fetus under these conditions.

It can be concluded from these studies that the treatment with CGRP during pregnancy, when progesterone levels are elevated, provides relief from the preeclampsia condition. These studies show that the basis for this effectiveness lies in the ability of the progestional agent to increase the effectiveness of CGRP to dilate blood vessels and thereby lower blood pressure as well as increase fetal-maternal perfusion, thereby increasing fetal survival rate (i.e., decrease the fetal mortality).

The selective effects of CGRP during pregnancy but not in postpartum is surprisingly dramatic. There is no prior evidence existing to suggest the effects of CGRP during pregnancy. The studies indicate that Progestins increase the effector system for CGRP.

The method of treatment employed in this invention can also be employed for the treatment of hypertension (in both females and males), climacteric disorders (hot flushes, mood swings) in menopausal women, thrombotic disorders, menstrual disorders (dysmenorrhea, functional uterine bleeding), and hemorrhage, etc., following the dosage regimen described herein, and most importantly to prevent premature/preterm labor.

Without further elaboration, it is believed that one skilled in the art can, using the preceding description, utilize the present invention to its fullest extent. The preferred specific embodiments are, therefore, to be construed as merely illustrative, and not limitative of the disclosure in any way whatsoever.

EXAMPLE 1

Treatment of Preeclampsia, CGRP and Progesterone

To a pregnant human female (e.g., 20–40 years; 60–80 kg) usually in her second half of pregnancy and displaying the symptoms of preeclampsia, including hypertension (above 140 mm systolic and above 90 mm diastolic), edema and proteinuria 0.1–0.5 nmol/kg/24/hr of CGRP should be administered parenterally and until symptoms are ameliorated. Thereafter 0.1–0.2 nmol/kg/24 hr of CGRP parenterally and 60 mg of progesterone per os are administered daily whenever the diastolic pressure rises above 80 mm; with increasing doses of CGRP to from up to a 1 nmol/kg/24 hr parenterally daily until remission of the symptoms again occurs.

EXAMPLE 2

Treatment of Preeclampsia, CGRP, Progesterone and NO

To a human female comparable to and displaying the same symptoms as the one described in Example 1, administer daily 0.1–0.5 nmol of CGRP, or CGRP/adrenomedullin peptide or receptor-based analogues in an equivalent doses, and in combination with 200 mg of micronized progesterone per os daily in three divided doses with or without nitric oxide substrate or donor following the same protocol, until the symptoms are ameliorated.

EXAMPLE 3

Prevention of Premature/Preterm Labor

To a human female with signs and symptoms of preeclampsia or eclampsia of pregnancy or preterm/premature labor, 0.1–0.5 nmol/kg/24 hr doses of CGRP or CGRP/adrenomedullin peptide or receptor-based analogues should be administered in equivalent doses with or without supplementation with a progestin, a NO substrate or donor, or a cyclooxygenase inhibitor as described in the methodology.

The preceeding examples can be repeated with similar success by substituting the generically or specifically described reactants and/or operating conditions of this invention for those used in the preceding examples. All the references cited above are incorporated by reference herein for the reasons cited.

From the foregoing description, one skilled in the art can easily ascertain the essential characteristics of this invention, and without departing from the spirit and scope thereof, can make various changes and modifications of the invention to adapt it to various usage and conditions.

The entire disclosure of all applications, patents and publications, cited above and below are hereby incorporated by reference.

What is claimed is:

1. A method of treating preeclampsia and eclampsia of pregnancy in a pregnant female mammal comprising administering to the afflicted female a therapeutically effective amount of CGRP (calcitonin gene related peptide) in the presence of progesterone.

2. The method of claim 1 where the amount is bioequivalent to 0.1–0.5 nmol/kg/24 hr of CGRP.

3. The method of claim 1 where the progesterone is in an amount bioequivalent to 50–300 mg of injected progesterone.

4. The method of claim 1 or 2 further comprising administration of an amount of L-arginine.

5. The method of claim 4 where the amount of L-arginine is effective to raise L-arginine blood level at least about 1 mM above normally circulating levels.

6. The method of claim 4 where the amount of L-arginine is about 0.5 to about 10 g/day and is orally administered.

7. The method of claim 1 or 2 further comprising administration of a nitric oxide donor.

8. The method of claim 7 where the nitric oxide donor is at least one of sodium nitroprusside, nitroglycerin, isosorbidmonoonittate, and isosorbiddinitrate.

9. The method of claim 1 or 2 further comprising administration of at least one of a cyclooxygenase inhibitor, a $PGI_2$ (prostacyclin)-mimetic, a thromboxane ($TXA_2$) inhibitor, a compound possessing $TXA_2$-antagonistic and $PGI_2$-memetic activities, and a $TXA_2$ antagonist, in amounts effective to ameliorate symptoms of preeclampsia or eclampsia.

10. The method of claim 1 where the CGRP is αCGRP or βCGRP.

11. The method of claim 1, wherein the female mammal is a human.

12. The method of claim 1, wherein the female mammal is a human and at least one of L-arginine and a nitric oxide donor is coadministered.

13. The method of claim 1, wherein a cyclooxygenase inhibitor is coadministered.

14. The method of claim 1, wherein the female mammal is a human and arginine or a nitric oxide donor is coadministered.

15. The method of claim 1, wherein the female mammal is a human and a cyclooxygenase inhibitor is coadministered.

16. The method of claim 1, wherein the female mammal is a human and at least one of L-arginine or a nitric oxide donor or a cyclooxygenase inhibitor is coadministered.

17. The method of claim 1, wherein the female mammal is a human and a $PGI_2$-mimetic is coadministered.

18. A pharmaceutical composition comprising a therapeutically effective amount of CGRP and progesterone.

19. A pharmaceutical composition comprising a therapeutically effective amount of CGRP, progesterone and at least one of L-arginine or a nitric oxide donor.

20. The composition of claim 18 further comprising at least one of L-arginine and a nitric oxide donor.

21. The composition of claim 18 further also comprising at least one of a cyclooxygenase inhibitor or a $PGI_2$-mimetic, a thromboxane ($TXA_2$) inhibitor, a compound possessing $TXA_2$-agonistic or $TXA_2$-inhibiting properties, a compound possessing $TXA_2$-antagonistic or $PGI_2$-mimetic activities or a $TXA_2$ antagonist.

22. The composition of claim 21 wherein a nitric oxide donor or L-arginine are in amounts effective to ameliorate the symptoms of preeclampsia, or eclampsia in a pregnant female mammal when administered to a female mammal.

23. The composition of claim 22 wherein the amounts of the CGRP and L-arginine or nitric oxide donor are effective to raise the blood level of circulating CGRP to at least about 15 pmol/L above the normally 5–25 pmol/L circulating levels, raise blood L-arginine levels by 3–4 mmolar; or results in donor levels of about 1 to 1000 mmolar, and an amount of progesterone bioequivalent to 50–300 mg of injected progesterone.

24. The method of claim 13, 15 or 16, wherein the cyclooxygenase inhibitor inhibits cyclooxygenase-I or -II.

25. The method of claim 24 where the inhibitor is aspirin or indomethacin.

26. The composition of claim 21 wherein the $PGI_2$-mimetic is iloprost or cicaprost.

27. The composition according to claim 18 further comprising a cyclooxygenase inhibitor.

28. The composition according to claim 18 or 19 further comprising a $PGI_2$-mimetic.

29. The composition according to claim 18 or 19 further comprising a thromboxane inhibitor.

30. The composition according to claim 18 further comprising L-arginine.

31. The composition according to claim 18, further comprising a nitric oxide donor.

32. The composition according to claim 31, wherein the nitric oxide donor is sodium nitroprusside, nitroglycerin, isosorbidmononitrate or isosorbiddinitrate.

* * * * *

UNITED STATES PATENT AND TRADEMARK OFFICE
CERTIFICATE OF CORRECTION

PATENT NO. : 5,910,482
DATED : June 8, 1999
INVENTOR(S) : Chandrasekhar Yallampalli and Sunil J. Wimalawansa It is certified that error appears in the above-indentified patent and that said Letters Patent is hereby corrected as shown below:

Title page, item [54], ln. 2, delete the comma after "PREECLAMPSIA" and insert the word --AND--.

At col. 1, ln. 2, delete the comma after the word "PREECLAMPSIA" and insert the word --AND--.

At col. 13, ln. 31 (claim 8), delete "isosorbidmonoonittate" and insert --isosorbidmononitrate-- therefor.

At col. 14, ln. 33 (claim 23), delete "mmolar" and insert --nmolar-- therefor.

Signed and Sealed this

Twenty-third Day of November, 1999

Attest:

Q. TODD DICKINSON

*Attesting Officer*  *Acting Commissioner of Patents and Trademarks*

```
SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
        (A) LENGTH: 37 amino acids
        (B) TYPE: amino acid
        (C) STRANDEDNESS:
        (D) TOPOLOGY: linear (xi) SEQUENCE DESCRIPTION: SEQ ID NO:1:

Ala Cys Asp Thr Ala Thr Cys Val Thr His Arg Leu Ala Gly Leu Leu
    1               5                   10                  15

Ser Arg Ser Gly Gly Val Val Lys Asn Asn Phe Val Pro Thr Asn Val
                20                  25                  30

Gly Ser Lys Ala Phe
            35

(2) INFORMATION FOR SEQ ID NO:2:

(i) SEQUENCE CHARACTERISTICS:
        (A) LENGTH: 37 amino acids
        (B) TYPE: amino acid
        (C) STRANDEDNESS:
        (D) TOPOLOGY: linear (xi) SEQUENCE DESCRIPTION: SEQ ID NO:2:

Ala Cys Asn Thr Ala Thr Cys Val Thr His Arg Leu Ala Gly Leu Leu
    1               5                   10                  15
```

```
Ser Arg Ser Gly Gly Met Val Lys Ser Asn Phe Val Pro Thr Asn Val
            20                  25                  30

Gly Ser Lys Ala Phe
            35
```